(12) United States Patent
Wang et al.

(10) Patent No.: US 10,431,328 B1
(45) Date of Patent: Oct. 1, 2019

(54) METHOD AND SYSTEM FOR ANATOMICAL TREE STRUCTURE ANALYSIS

(71) Applicant: BEIJING CURACLOUD TECHNOLOGY CO., LTD., Beijing (CN)

(72) Inventors: Xin Wang, Seattle, WA (US); Youbing Yin, Kenmore, WA (US); Kunlin Cao, Kenmore, WA (US); Junjie Bai, Seattle, WA (US); Yi Lu, Seattle, WA (US); Bin Ouyang, Shenzhen (CN); Qi Song, Seattle, WA (US)

(73) Assignee: BEIJING CURACLOUD TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/138,946

(22) Filed: Sep. 21, 2018

Related U.S. Application Data

(60) Provisional application No. 62/679,868, filed on Jun. 3, 2018.

(51) Int. Cl.
| | |
|---|---|
| *G01N 33/48* | (2006.01) |
| *G01N 33/50* | (2006.01) |
| *G16B 45/00* | (2019.01) |
| *G06N 3/04* | (2006.01) |
| *G16B 5/00* | (2019.01) |
| *G16B 40/00* | (2019.01) |

(52) U.S. Cl.
CPC ............. *G16B 45/00* (2019.02); *G06N 3/049* (2013.01); *G16B 5/00* (2019.02); *G16B 40/00* (2019.02)

(58) Field of Classification Search
None
See application file for complete search history.

(56) References Cited

PUBLICATIONS

Cruse et al. MMC—a recurrent neutral network which can be used as manipulable body model. In "From Animals to Animats," pp. 381-389. (Year: 1998).*

(Continued)

*Primary Examiner* — Russell S Negin
(74) *Attorney, Agent, or Firm* — Bayes PLLC

(57) ABSTRACT

The present disclosure is directed to a computer-implemented method and system for anatomical tree structure analysis. The method may begin with receiving a task of the anatomical tree structure analysis. Then, a set of positions in the anatomical tree structure may be set or received, by a processor, as the sampling positions for model inputs and model outputs. Then model inputs may be determined, by the processor, at the sampling positions on the basis of the task. An encoder may be selected, by the processor, for each position of the set of positions on the basis of the task. The encoder may be configured to receive a model input at each position and extract features for the corresponding position. After that, a tree structured recurrent neural network (RNN) may be constructed by the processor with nodes corresponding to the set of positions and connected with the respective encoders. An RNN unit for each node may be selected on the basis of the task and an information propagation among the nodes may be set on the basis of the spatial constraints of the set of positions in the anatomical tree structure. The generated treed structured RNN may be provided for performing the task of the anatomical tree structure analysis.

20 Claims, 9 Drawing Sheets

(56) References Cited

PUBLICATIONS

Kalchbrenner et al. A convolutional neural network for modelling sentences. arXiv, 1404.2188v1, 11 pages. (Year: 2014).*
Cho et al. Learning phrase representations using RNN encoder-decoder for statistical machine translation. arXiv:1406.1078v3, 15 pages. (Year: 2014).*

* cited by examiner

METHOD AND SYSTEM FOR ANATOMICAL TREE STRUCTURE ANALYSIS

CROSS-REFERENCE TO RELATED APPLICATION

This application claims the benefit of priority to U.S. Provisional Application No. 62/679,868, filed on Jun. 3, 2018, the entire content of which are incorporated herein by reference.

TECHNICAL FIELD

The disclosure generally relates to image processing and analysis. More specifically, this disclosure relates to a method and system for anatomical tree structure analysis.

BACKGROUND

Anatomical tree structures commonly exist in human bodies, including human airways, blood vessels (such as arteries, veins, capillaries, etc.), nervous tissues, and breast ducts extending from the nipple, etc. Recent technological advances in medical imaging (CT, MRI, DSA imaging, etc.) make it possible to non-invasively acquire medical images of different dimensions, such as 2D, 3D, 4D, etc., containing the anatomical tree structure. Clinicians rely on radiologists' interpretation of the medical images to perform various disease diagnosis, including but not limited to abnormality detection (such as lumen stenosis/widening detection, calcification detection, plaque detection, etc.), abnormality classification (such as plaque type classification among normal, stenosis, widening, calcified plaque, non-calcified plaque and mixed plaque, etc.), parameter quantification (such as abnormality (narrowing, widening, calcification) degree quantification, physiological measurement (diameter, area, flow rate, etc.) estimation, fractional flow reserve estimation), tree branch labeling (such as labeling the extracted branches with their anatomical names), and segmentation (such as vessel lumen segmentation), etc.

Usually, in clinical practice, the anatomical tree structure analysis is manually performed by a radiologist, which is labor-intensive and time-consuming, and the results may be subjective. Therefore, automated/semi-automated computer implemented anatomical tree structure analysis may be adopted to assist the radiologists in improving the efficiency, accuracy, and consistency of the image analysis.

Although machine learning-based algorithms have been introduced for such semi-automated or automated image analysis of the anatomical tree structure, these algorithms typically rely on the local features of a single centerline point or sequential centerline points sampled along individual branches, and thus are only able to achieve single point or sequential analysis. More importantly, for the same anatomical tree structure, these algorithms have to analyze the respective branches asynchronously, which may obtain inconsistent analysis results in the bifurcation regions and overlapped branch regions, reducing the analysis accuracy and efficiency.

The present disclosure is proposed to address the above concerns.

SUMMARY

The present disclosure intends to provide a method and system for anatomical tree structure analysis, in which a tree structure based model may be generated for a particular task of the anatomical tree structure analysis. The generated model does not consider the features of the respective sampling positions in the anatomical tree structure independently. Instead, it embeds tree structured spatial relationships among the nodes of the recurrent neural network portion (especially the information propagation among the nodes) in the model, and takes into account the global dependency of the sampling positions in the whole tree structure. Thus, the generated model may improve the analysis accuracy and efficiency. Besides, the generated model may obtain the analysis results for all the sampling positions throughout the branches in the anatomical tree structure simultaneously, to avoid potential errors caused by asynchronous analysis of the branches.

In one aspect, the present disclosure is directed to a computer-implemented method and system for an anatomical tree structure analysis. The method may begin with receiving a task of the anatomical tree structure analysis. Then, a set of positions in the anatomical tree structure may be set, by a processor, as the sampling positions for model inputs and model outputs. Then a model input may be determined, by the processor, at each position among the set of positions on the basis of the task. An encoder may be selected, by the processor, for each position on the basis of the task. The encoder may be configured to receive the model input at each position and extract features for the corresponding sampling position. After that, a tree structured recurrent neural network (RNN) may be constructed by the processor with nodes corresponding to the set of positions and connected with the respective encoders. The generated model is therefore adaptive to the task. AN RNN unit for each node may be selected on the basis of the task and an information propagation among the nodes may be set on the basis of the spatial constraints of the set of positions in the anatomical tree structure. The tree structured RNN may be provided for performing the task of the anatomical tree structure analysis.

In another aspect, the present disclosure is directed to a computer-implemented method for anatomical tree structure analysis. An anatomical tree structure image acquired by an image acquisition device may be received. Then the analysis model for the specific task of the anatomical tree structure analysis may be received. The analysis model may be constructed by connecting encoders for a set of positions in the anatomical tree structure with nodes of a tree structured recurrent neural network (RNN). The nodes may correspond to the set of positions. The model input, the encoder, and an RNN unit of each node are selected based on the task, and an information propagation among the nodes are based on the spatial constraints of the set of positions in the anatomical tree structure. The model inputs at the set of positions may be calculated, by a processor, from the anatomical tree structure image. The specific task of the anatomical tree structure analysis then may be performed, by the processor, by using the analysis model on the basis of the calculated model inputs.

In another aspect, the present disclosure is directed to a system for an anatomical tree structure analysis. The system may include an interface configured to acquire an anatomical tree structure image, and a processor. The processor may be configured to receive a task of the anatomical tree structure analysis. The processor may be further configured to set a set of positions in the anatomical tree structure and determine a model input at each position among the set of positions on the basis of the task. The processor may be configured to select an encoder for each position on the basis of the task, with the encoder configured to receive the model input at each position and extract features for the corresponding position. The processor may be configured to construct a tree structured RNN with nodes corresponding to the set of positions, by selecting an RNN unit for each node on the basis of the task and setting an information propagation among the nodes on the basis of the spatial constraints of the set of positions in the anatomical tree structure. The processor may be configured to connect the nodes of the tree structured RNN with the respective encoders. The processor may be further configured to provide the tree structured RNN for performing the task of the anatomical tree structure analysis.

In another aspect, the present disclosure is directed to a non-transitory computer readable medium having instructions stored thereon. The instructions, when executed by the processor, may perform the method for an anatomical tree structure analysis as described above.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, device, or non-transitory computer readable medium having instructions thereon for implementing the method.

DETAILED DESCRIPTION

Consistent with the present disclosure, the technical term "tree structure" may refer to one or more branches. The technical term "branch" refers to one of the physiological tubes (e.g. vessel tubes) stemming from a bifurcation point. The technical term "path" refers to a pass from the inlet to an outlet of the anatomical tree structure.

Figure 1:
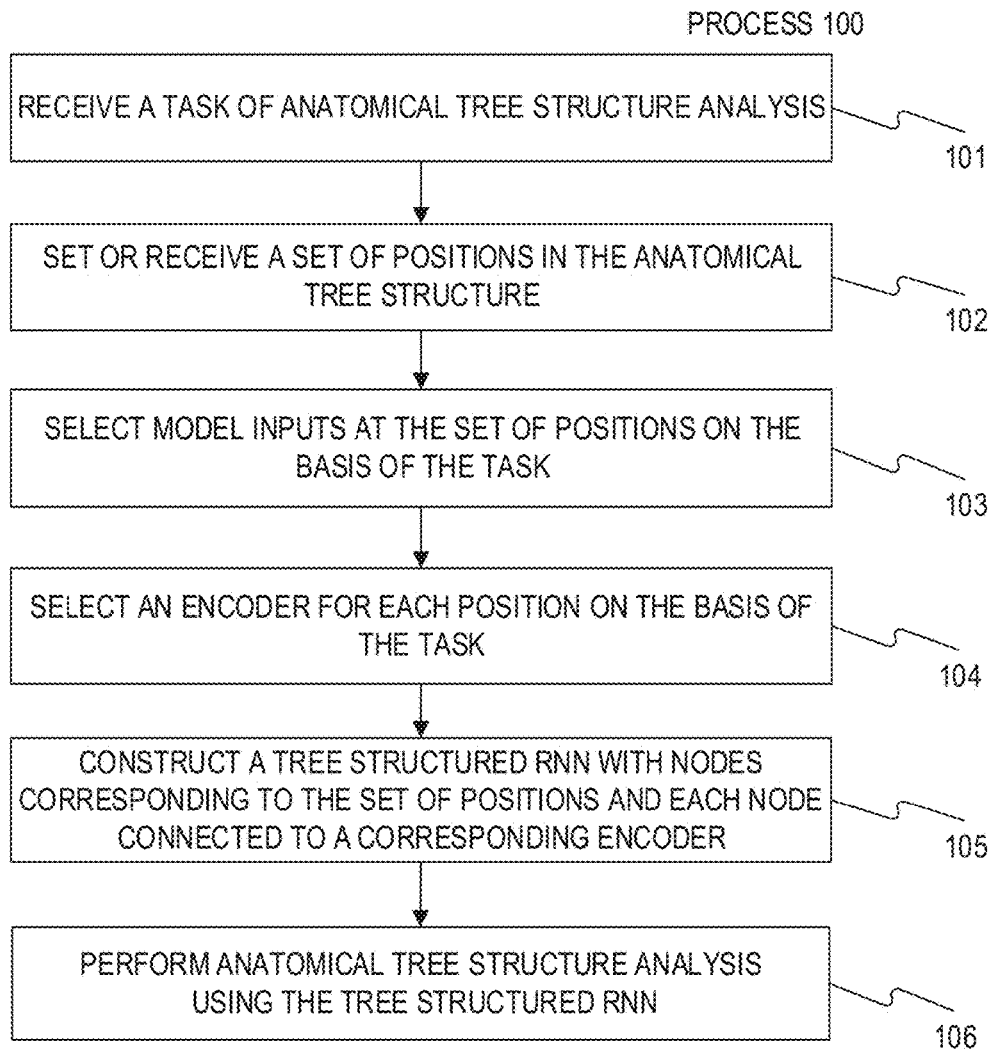
FIG. 1 illustrates an exemplary computer-implemented process for anatomical tree structure analysis, according to an embodiment of present disclosure.

FIG. 1 illustrates an exemplary computer-implemented method 100 for anatomical tree structure analysis, according to an embodiment of present disclosure. As shown in FIG. 1, the method 100 begins with receiving a task of anatomical tree structure analysis (step 101). In some embodiments, the task of the anatomical tree structure analysis may be assigned by a user by selecting the analysis task options in a menu of the image analysis software. For example, when the user checks the "FFR prediction" option, the "FFR prediction" task is received at step 101. In some embodiments, the task of anatomical tree structure analysis may be customized for the user with the image analysis software. As an example, as a user request, a vessel plaque segmentation task may be customized, and the customized vessel plaque segmentation task may be received at step 101. In some embodiments, the method 100 may be implemented by the image analysis software to perform adaptive image analysis functions. Unlike the current image analysis software with a fixed framework of image analysis model, the image analysis software implementing the method 100 allows adaptive modeling for variable analysis tasks.

In step 102, a set of positions in the anatomical tree structure may be set or received, by a processor, as the sampling positions for model inputs and model outputs. In some embodiments, the set of positions may be set automatically by a processor. As an example, upon receiving the vessel tree structure image, the processor may perform vessel wall and centerline (as an example of the skeleton line) extraction and set the sampling positions along the centerline. As an example, the bifurcation points of the centerline may be included, which usually carry anatomical meaningful information and assist the tree structured RNN in accurately accounting for the global dependency of the positions in the whole tree. In some embodiments, the processor may extract the branches and the bifurcation points in the vessel tree structure and set at least one point in each branch in addition to the bifurcation points as the set of sampling positions. In this manner, the tree structured RNN may accurately and completely take into account the global dependency of the positions in the whole tree.

In some embodiments, the set of positions may be set semi-automatically by the processor. As an example, the user (e.g. a radiologist, physician, clinician, etc.) may manually assign the number of the points in each branch besides the bifurcation points or assign the analysis resolution (e.g., 0.2 mm), and the processor may set the sampling positions accordingly.

In some embodiments, the set of positions may be set manually by the user. As an example, an anatomical tree structure image may be acquired and presented to the user for him/her to manually set the sampling positions. As another example, the skeleton line of the anatomical tree structure may be extracted and present to the user for him/her to manually set the sampling positions along the skeleton line. In this manner, the user may incorporate the points of interest, such as the candidate stenosis, the bifurcation points, etc., into the sampling positions, to ensure that the model may obtain the analysis results at the sampling positions as needed by the diagnosis.

In step 103, model inputs may be selected, by the processor at the sampling positions on the basis of the task. For neural network-based analyzing model, various model inputs may be adopted, including but not limited to features (geometrical features, flow features, etc.) or image patches along the skeleton line of the anatomical tree structure. In step 103, proper type of model inputs may be selected on the basis of the particular task. As an example, under the condition that the task is any one of abnormality detection (e.g., disease detection), abnormality classification (e.g., disease labeling), parameter quantification (e.g., to quantify continuous measurements associated with the anatomical tree structure), or labeling (labeling the extracted branches with their anatomical names). Image patches or feature vectors may be selected as the model inputs. As another example, under the condition that the task is segmentation (e.g., tumor segmentation, stenosis segmentation, etc.), image patches may be adopted as the model inputs.

In step 104, an encoder may be selected, by the processor, for each position of the set of positions on the basis of the task. The encoder may be configured to receive the model inputs at each position and extract features for the corresponding position. The encoder may be used to extract features for the model input at the corresponding sampling position, from which local-relevant information may be extracted. The features may form a feature vector for abnormality detection, abnormality classification, or parameter quantification tasks, and/or may be a feature map for segmentation task. In contrast to using fixed feature as model inputs, the disclosed encoder may encode hidden feature information, especially the higher-level feature information. In some embodiments, to perform tasks such as abnormality detection, abnormality classification, or parameter quantification, at least one of convolutional neural network (CNN), fully convolutional neural network (FCN), and multi-layer perceptron (MLP) may be selected as the encoder. In some embodiments, under the condition that the task is segmentation, CNN or FCN may be selected as the encoder.

After that, in step 105, a tree structured recurrent neural network (RNN) may be constructed by the processor with nodes corresponding to the set of positions. In some embodiments, proper RNN units may be selected for each node on the basis of the task. As an example, to perform tasks such as abnormality detection, abnormality classification, or parameter quantification, long short-term memory (LSTM) or gate recurrent unit (GRU) may be selected as an RNN unit. As another example, to perform a segmentation task, convolutional LSTM (CLSTM) or convolutional GRU (CGRU) may be selected as the RNN unit.

In some embodiments, the RNN model is designed to include an encoder to transform each model input to produce its feature vector/map representation, which will be passed onto the tree structured RNN model. As a result, the RNN model is adaptive for the task. In some embodiments, the RNN unit for each node may be selected on the basis of the task and the information propagation among the nodes may be set on the basis of the spatial constraints of the set of positions in the anatomical tree structure. With the information propagation among the nodes, the information from the sampling positions in the whole tree may be seamlessly integrated to improve accuracy of the image analysis. In addition, the analysis results for all the sampling positions may be obtained simultaneously, which further improves the analysis accuracy and efficiency by avoiding the additional time consumption as well as potential errors and inconsistencies caused by asynchronous processing of different positions/branches.

In some embodiments, the information propagation among the nodes of the tree structured RNN may be set to conform to the spatial constraints of the set of sampling positions in the anatomical tree structure. As an example, if two sampling positions are spatially connected in a vessel branch, the corresponding two nodes are connected. As another example, if a first sampling position and a second sampling position are located in two respective vessel branches and are connected with each other via a third sampling position at the bifurcation point, the third node corresponding to the third sampling position connects the first node corresponding to the first sampling position with the second node corresponding to the second sampling position. In some embodiments, bidirectional information propagation may be allowed between each pair of nodes corresponding to two adjacent positions in a path of the anatomical tree structure. Alternatively, unidirectional information propagation from distal side to root may be set between at least one pair of nodes corresponding to two adjacent positions in the path of the anatomical tree structure. In this manner, the node tree structure maintains the topology of the anatomical tree structure and simulates accurately the global physical acting mechanism of the points in the anatomical tree structure, which improves the analysis accuracy and efficiency of the analysis model.

In step 106, the analysis model generated adaptively may be used to implement variable anatomical tree structure analysis tasks. Specifically, an anatomical tree structure image may be acquired. As described above, the analysis model may be constructed by connecting encoders for a set of positions in the anatomical tree structure with the corresponding nodes of a tree structured recurrent neural network (RNN) with nodes corresponding to the set of positions, wherein model input, encoder, and RNN unit of each node are based on the task, and information propagation among the nodes are based on the spatial constraints of the set of positions in the anatomical tree structure. To apply the analysis model, model inputs at the set of positions may be calculated from the anatomical tree structure image acquired for the specific task of the anatomical tree structure analysis. The calculated model inputs are then input into the analysis model.

Figure 2:
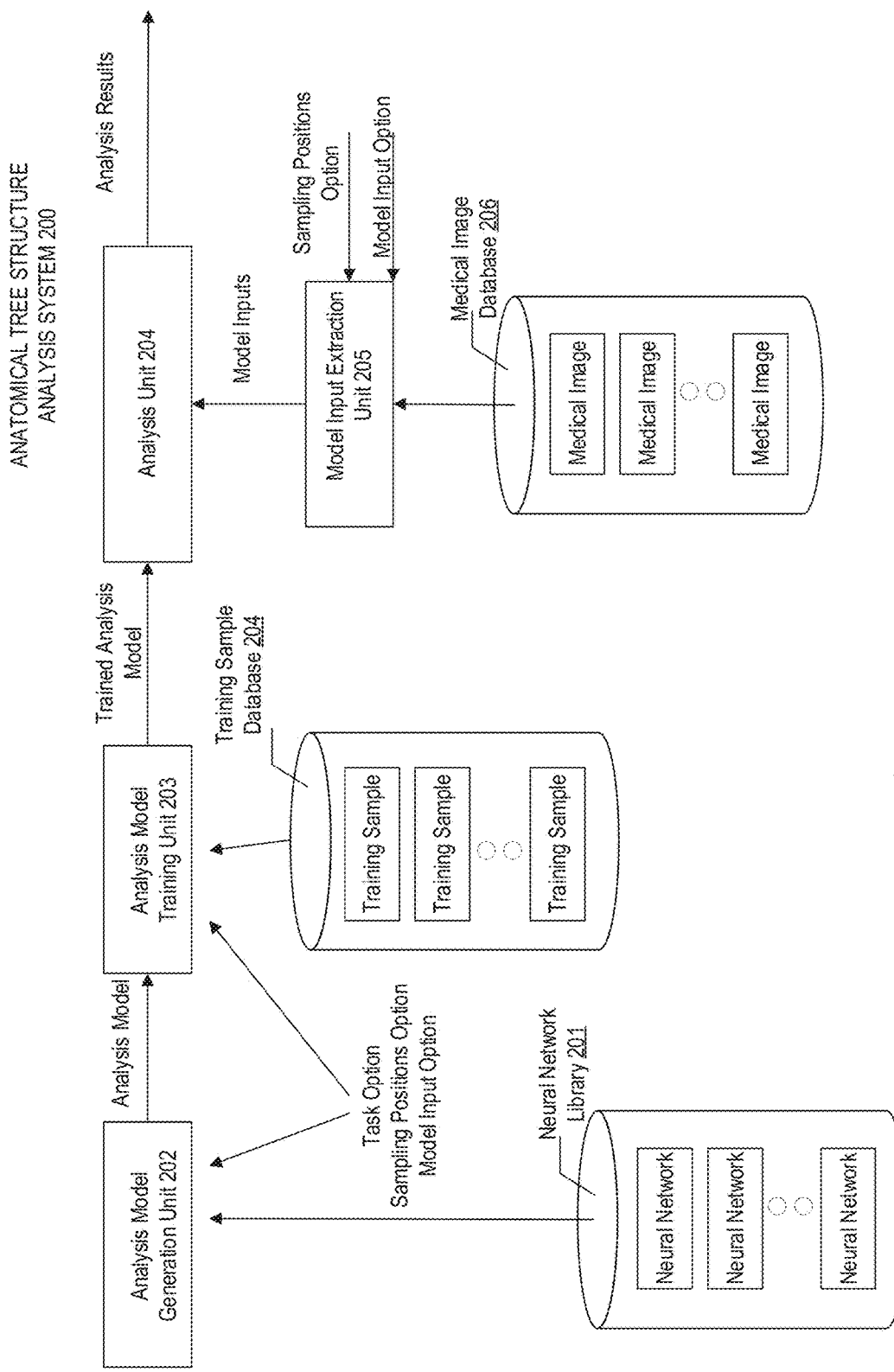
FIG. 2 illustrates an exemplary anatomical tree structure analysis system, according to an embodiment of present disclosure.

FIG. 2 illustrates an exemplary anatomical tree structure analysis system 200 according to an embodiment of present disclosure. As shown in FIG. 2, the anatomical tree structure analysis system 200 may include an analysis model generation unit 202, an analysis model training unit 203, and an analysis unit 204. The analysis model generation unit 202 may be configured to receive task option, sampling position option, and model input option, select and retrieve proper encoders and RNN units from the neural network library 201 based on the received options, and generate the analysis model with the retrieved encoders and RNN units. In some embodiments, analysis model may be comprised of an encoder connected with each node of the tree structured RNN model where the RNN nodes corresponding to the sampling positions. The retrieved encoders may be used for each node of the encoder portion, the retrieved RNN units may be used for each node of the tree structured RNN portion, and information propagation among the nodes of the tree structured RNN portion may be set on the basis of the spatial constraints of the sampling positions in the anatomical tree structure.

In some embodiments, the analysis model may be transmitted from the analysis model generation unit 202 to the analysis model training unit 203 to be trained. In some embodiments, the analysis model training unit 203 may obtain corresponding training samples from the training sample database 204 on the basis of the task option, sampling position option, and model input option and train the analysis model with the obtained training samples. As an example, for the task option as "vessel stenosis label prediction," the sampling positions option as "centerline points at regular interval," and the model input option as "vessel diameter," vessel images annotated with vessel diameter and stenosis labels may be obtained from the training sample database 204 as training samples to train the analysis model.

In some embodiments, the trained analysis model may be transmitted from the analysis model training unit 203 to the analysis unit 204. The analysis unit 204 may receive model inputs from a model input extraction unit 205 and perform the analysis using the trained analysis model on the basis of the received model inputs. The model input extraction unit 205 may receive the sampling position option and model input option and extract the model inputs from medical images it receives from the medical image database 206 on the basis of the received sampling position options and model input options. As an example, for the sampling position option as "centerline points at regular interval" and the model input option as "vessel diameter," the model input extraction unit 205 may obtain vessel angiography images at different projection angles from the medical image database 206, reconstruct a 3D vessel model from the obtained vessel angiography images, and extract the vessel diameters at centerline points at the regular interval as the model inputs.

Figure 3:
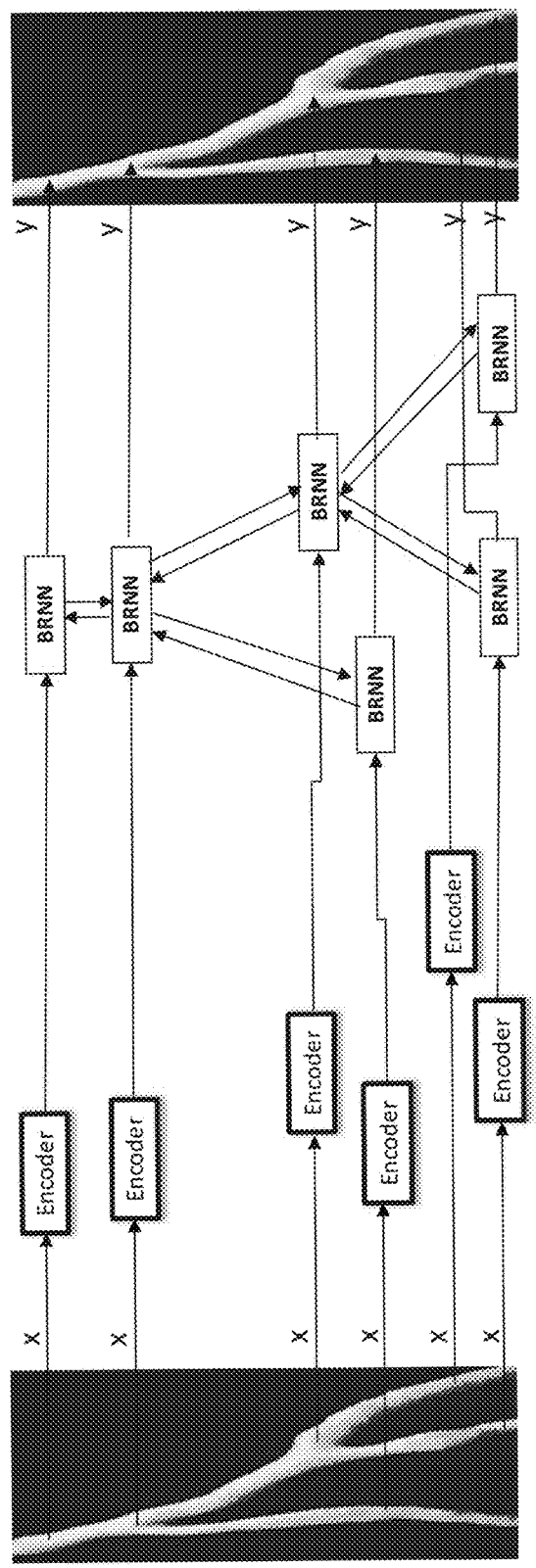
FIG. 3 illustrates an exemplary tree structure based learning model, according to an embodiment of present disclosure.

FIG. 3 illustrates an exemplary tree structure based learning model according to an embodiment of present disclosure. As shown in FIG. 3, the anatomical tree structure may be a vessel tree, and the model inputs x may be image patches or feature vectors at centerline points (sampling points) of the vessel tree. As an example, artificially defined feature vectors at centerline points of the vessel tree may be adopted as the model inputs x. As an example, the model inputs x may be vessel diameters at centerline sampling points of the vessel tree. The learning model is a combination of two portions to form an end-to-end network. One portion is the encoder portion and the other portion is a tree structured RNN. In some embodiments, the encoder is configured to construct a feature vector (or feature map) for each model input x, from which local-relevant higher-level feature information may be extracted. The tree structure RNN portion may be comprised of nodes corresponding to the centerline sampling points, with bi-directional RNN as the node. Feature information (such as feature vector or feature map) may be transmitted from each encoder to the corresponding node of the tree structure RNN portion. Bidirectional information propagation may be set between each pair of nodes corresponding to two adjacent centerline sampling points in a path of the vessel tree, to handle the spatial constraint in the vessel tree. The nodes of the tree structure RNN portion may integrate the feature information at all the centerline sampling points in the whole vessel tree, to make predictions (prediction result y) for all centerline sampling points in the vessel tree simultaneously. It may avoid potential errors caused by pre-processing or post-processing. As shown in FIG. 3, two bifurcation points along the centerline are incorporated into the sampling points. As an example, each branch of the vessel tree may include at least one sampling point other than the bifurcation points.

Figure 4:
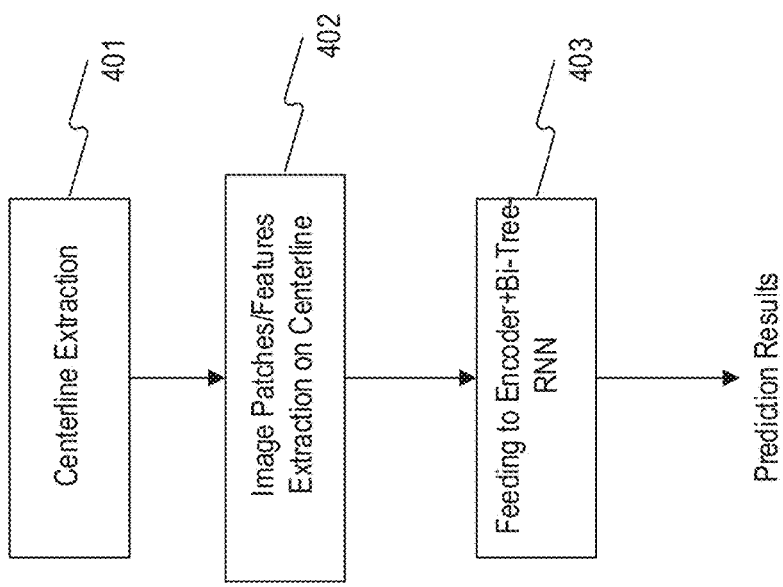
FIG. 4 illustrates an exemplary vessel stenosis degree prediction process, according to an embodiment of present disclosure.

FIG. 4 illustrates an exemplary vessel stenosis degree prediction process 400 according to an embodiment of present disclosure. The prediction process 400 begins with centerline extraction 401. In some embodiments, vessel images may be acquired using imaging devices, and centerline may be extracted from the acquired vessel images. Then, image patches or features may be extracted on the centerline (step 402) as the inputs of the prediction model comprised of encoders and bi-tree-RNN. If geometrical features along the centerline are used as the model inputs, centerline and vessel wall may be extracted from the acquired vessel images to reconstruct a 3D vessel model and extract the geometrical features along the centerline. The model inputs may be fed into the trained prediction model (step 403), to output prediction results of the vessel stenosis degree along the centerline.

Figure 5:
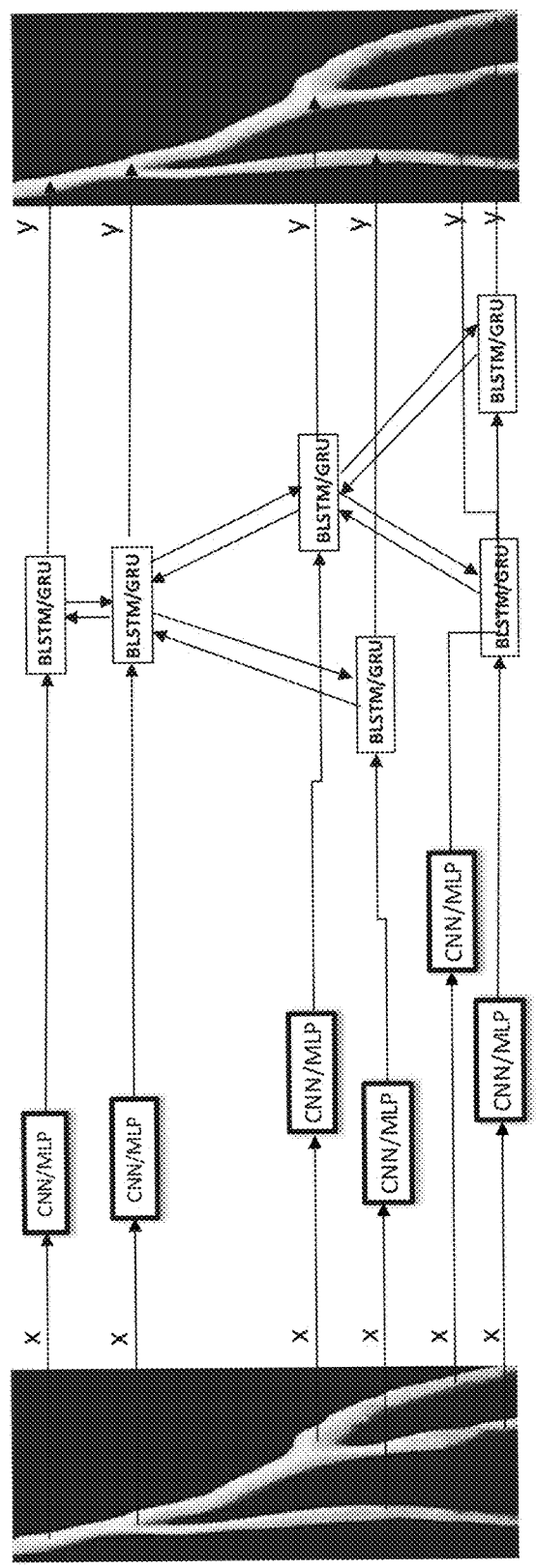
FIG. 5 illustrates an exemplary tree structure based learning model, according to an embodiment of present disclosure.

In some embodiments, an exemplary tree structure based learning model as shown in FIG. 5 may be used by the vessel stenosis degree prediction process 400. As shown in FIG. 5, x may be image patches or feature vectors, y may be continuous parameter values (e.g. vessel stenosis degree) along the vessel centerline, the encoder may be a CNN and/or an MLP, and the RNN may be a BLSTM and/or a GRU.

Figure 6:
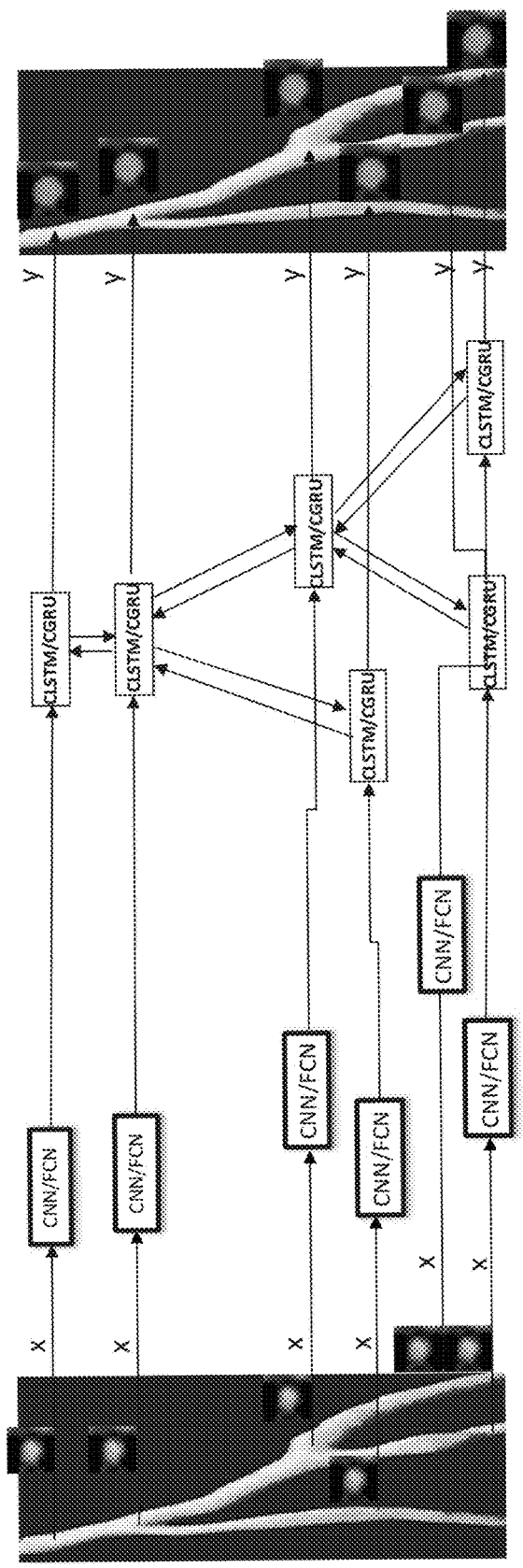
FIG. 6 illustrates an exemplary tree structure based learning model, according to an embodiment of present disclosure.

FIG. 6 illustrates an exemplary tree structure based learning model according to an embodiment of present disclosure. As shown in FIG. 6, x may be image patches, y may be segmentation masks, the encoder may be a CNN and/or an FCN, and the RNN may be a CLSTM and/or a CGRU. The learning model as shown in FIG. 6 may be used as segmentation model for image segmentation task, e.g. vessel stenosis segmentation process.

Figure 7:
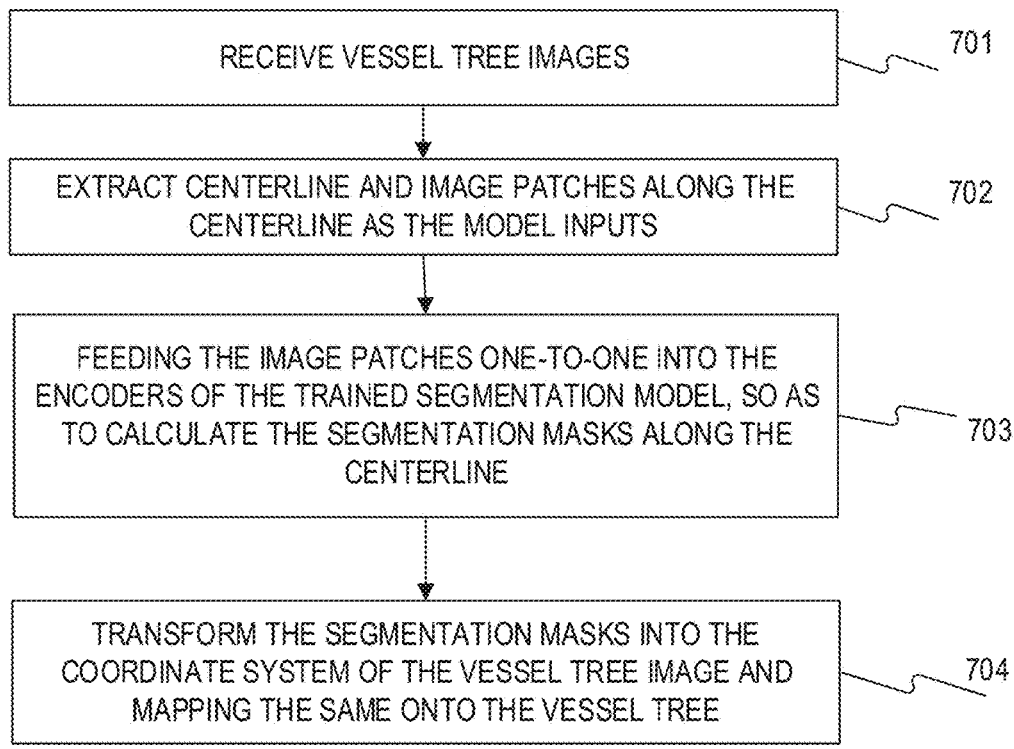
FIG. 7 illustrates an exemplary vessel stenosis segmentation process using a segmentation model, according to an embodiment of present disclosure.

FIG. 7 illustrates an exemplary vessel stenosis segmentation process 700 using a segmentation model generated by the method according to an embodiment of present disclosure. The vessel stenosis segmentation process 700 may be performed in an online manner, and may begin with receiving vessel tree images, which may be acquired and transmitted by various imaging devices (step 701). In step 702, a centerline may be extracted from the received vessel tree images and image patches may be extracted at sampling positions along the centerline as the model inputs. Then the image patches at the sampling positions along the centerline may be fed (one-to-one) into the encoders of the trained segmentation model, to calculate the segmentation masks at the sampling positions along the centerline as the model outputs (step 703). After that, the calculated segmentation masks may be transformed into a coordinate system of the vessel tree image and mapped onto the vessel tree (step 704), to present the segmentation results in an intuitive manner to the user. By means of the vessel stenosis segmentation process 700, the vessel stenosis segmentation may be performed from end to end automatically. That is, the user may input the acquired vessel tree images and receive the vessel stenosis segmentation result directly, which may be presented on a display.

Figure 8:
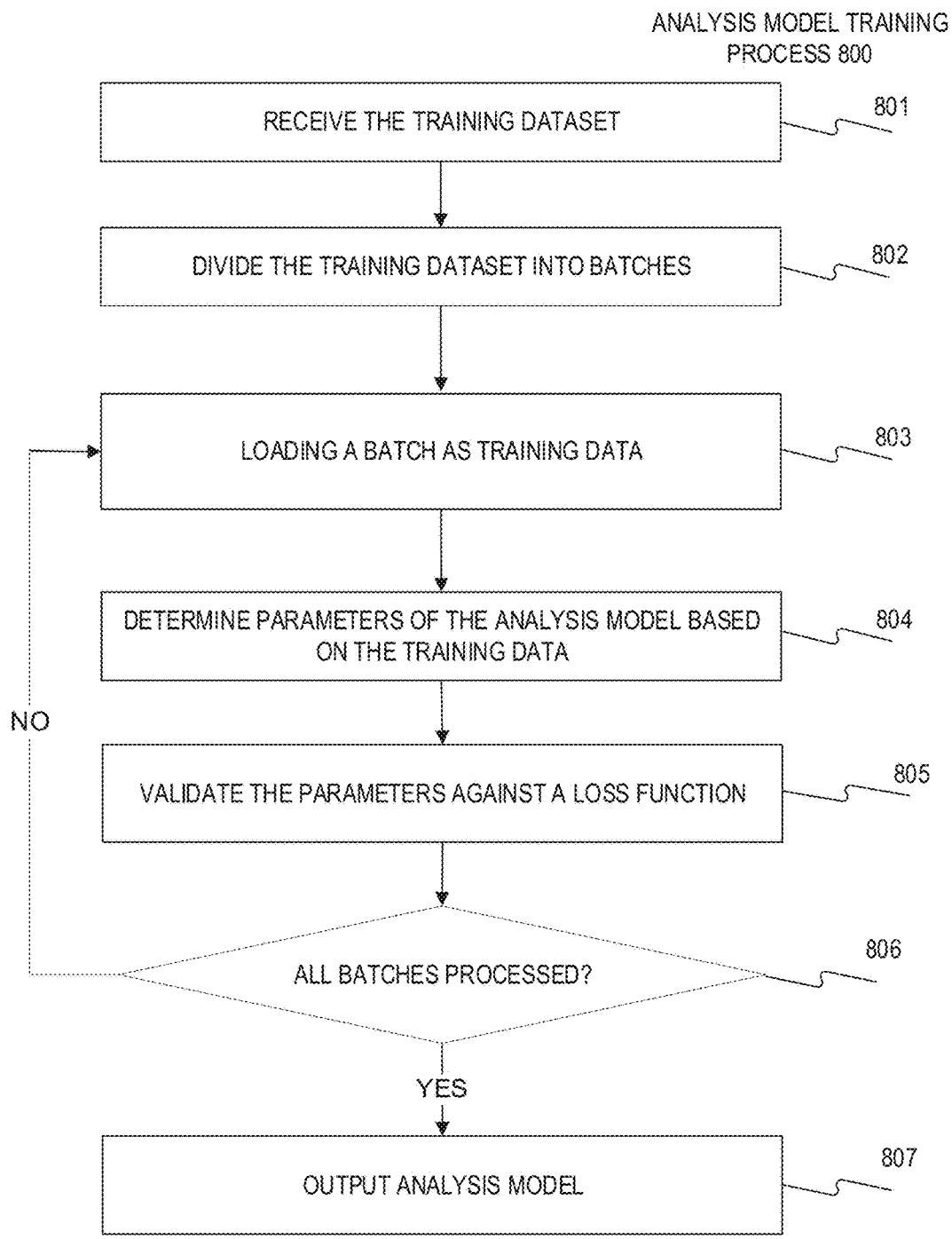
FIG. 8 illustrates an exemplary tree structure based learning model training process, according to an embodiment of present disclosure.

In some embodiments, the analysis model as described above may be trained in an off-line manner. FIG. 8 illustrates an exemplary analysis model training process 800, according to an embodiment of present disclosure. The process 800 may begin with receiving the training dataset (step 801). The received training dataset may be divided into batches (step 802), which may be individually loaded as a current training data (step 803). For example, the inputs of the analysis model may be denoted as $X=\{x_1, x_2, \ldots, x_t\}$ and the outputs of the analysis model may be denoted as $Y=\{y_1, y_2, \ldots, y_t\}$, respectively. For different image analysis tasks, inputs X may be image patches or feature vectors extracted from the anatomical tree structure at centerline points, and Y may be disease class labels, continuous measurements, segmentation mask, etc.

The parameters of the analysis model may be determined based on the batch of training data (step 804) and validated against a loss function (step 805) to be optimized for the batch of training data. As described above, the analysis model may be constructed by connecting an encoder with a corresponding node of a tree structured RNN. The analysis model thus may contain parameters (V, W) with parameters V for the encoder portion and parameters W for the tree structured RNN. In some embodiments, the parameters (V, W) may be jointly optimized by minimizing a loss function. As an example, the loss function may be the mean square error of the ground truth outputs 9 and the model output values $y_t$ at each position t within the batch. In some embodiments, the analysis model may be trained using gradient descent related methods to optimize the loss function with respect to all parameters (V, W) over each batch. As an example, for each batch, the mean square error may be calculated for each training sample in the batch, and gradient may be calculated based on the same and averaged. The analysis model, especially its parameters, may be updated based on the averaged gradient. Although gradient descent related methods and mean square error are disclosed as examples, other functions may be adopted including but not limited to cross entropy, etc., and other parameter optimizing methods may also be adopted, including but not limited to adaptive moment estimation, etc. Upon confirmation that all batches are processed in step 806, the analysis model, whose parameter have been optimized over all the batches, may be output (step 807).

The process 800 may adopt a mini-batch gradient descent method as an example. As an alternative, it may also adopt gradient descent or stochastic gradient descent methods. The mini-batch gradient descent method may achieve more robust convergence meanwhile efficiently avoiding local optimization with a relatively high computing efficiency. Besides, the memory does not need to load large amounts of training dataset for medical image analysis as a whole. Instead, the training samples may be loaded in batches, which relieves the working load of the memory and improves its working efficiency.

Figure 9:
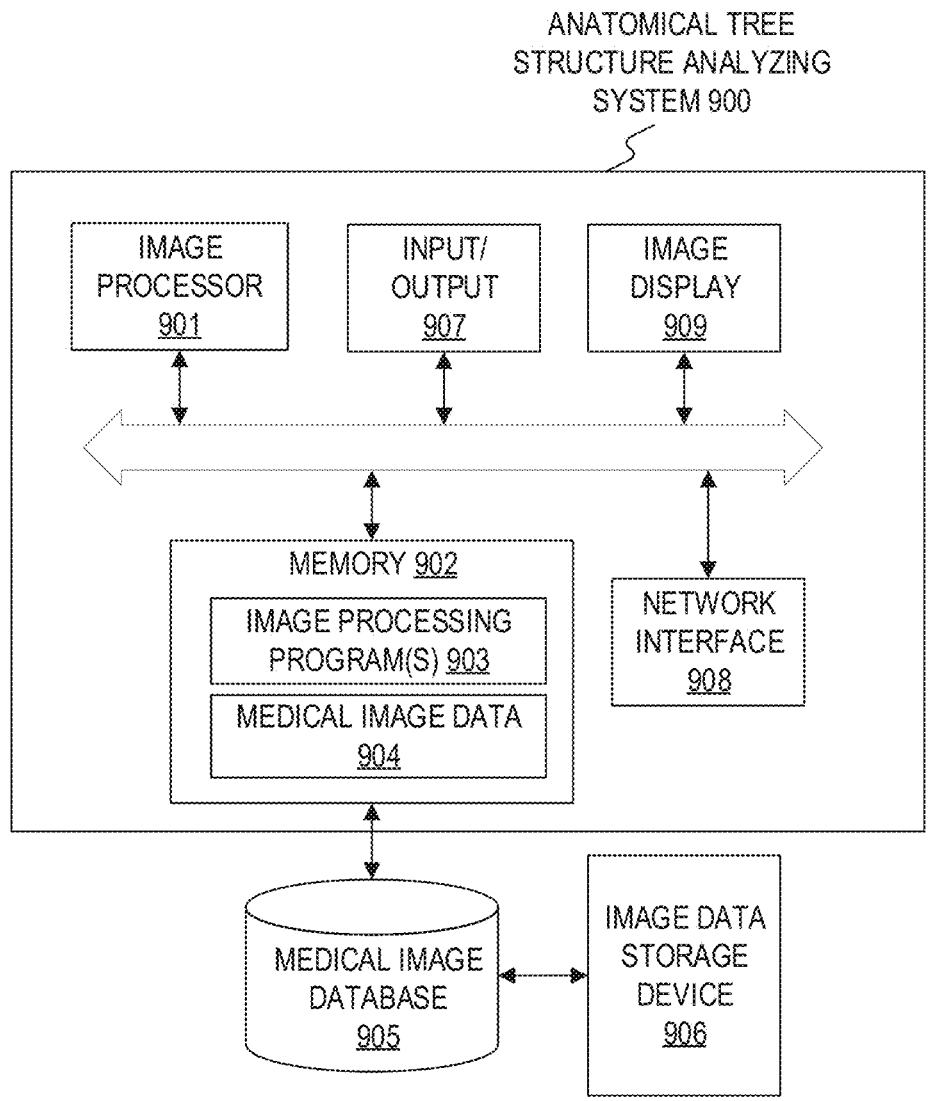
FIG. 9 depicts a block diagram illustrating an exemplary anatomical tree structure analyzing system, according to an embodiment of present disclosure.

FIG. 9 illustrates a block diagram of an exemplary anatomical tree structure analyzing system 900 according to an embodiment of present disclosure. The anatomical tree structure analyzing system 900 may include a network interface 908, by means of which the anatomical tree structure analyzing system 900 may be connected to the network (not shown), such as but not limited to the local area network in the hospital or the Internet. The network can connect the anatomical tree structure analyzing system 900 with external devices such as an image acquisition device (not shown), medical image database 905, and an image data storage device 906. An image acquisition device may be any type of imaging modalities, such as but not limited to CT, digital subtraction angiography (DSA), MRI, functional MRI, dynamic contrast enhanced MRI, diffusion MRI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging.

In some embodiments, the anatomical tree structure analyzing device 900 may be a dedicated intelligent device or a general purpose intelligent device. For example, the device 900 may be a computer customized for image data acquisition and image data processing tasks, or a server placed in the cloud. For example, the device 900 may be integrated into the image acquisition device. Optionally, the image processing program(s) 903 in the device 900 may include or cooperate with a 3D reconstruction unit for reconstructing the 3D model of the vessel on the basis of the 2D vessel images acquired by the image acquisition device, and extract geometrical features from the 3D model at a set of centerline points as image analysis model inputs $X=\{x_1, x_2, \ldots, x_t\}$.

The anatomical tree structure analyzing system 900 may include an image processor 901 and a memory 902, and may additionally include at least one of an input/output 907 and an image display 909.

The image processor 901 may be a processing device that includes one or more processing devices, such as a microprocessor, a central processing unit (CPU), a graphics processing unit (GPU), and the like. More specifically, the image processor 901 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 901 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 901 may be a special-purpose processor, rather than a general-purpose processor. The image processor 901 may include one or more known processing devices, such as a microprocessor from the Pentium™, Core™ Xeon™, or Itanium® family manufactured by Intel™, the Turion™, Athlon™, Sempron™ Opteron™, FX™, Phenom™ family manufactured by AMD™, or any of various processors manufactured by Sun Microsystems. The image processor 901 may also include graphical processing units such as a GPU from the GeForce®, Quadro®, Tesla® family manufactured by Nvidia™, GMA, Iris™ family manufactured by Intel™, or the Radeon™ family manufactured by AMD™. The image processor 901 may also include accelerated processing units such as the Desktop A-4 (9, 9) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to, or to manipulate any other type of data consistent with the disclosed embodiments. In addition, the term "processor" or "image processor" may include more than one processor, for example, a multi-core design or a plurality of processors each having a multi-core design. The image processor 901 can execute sequences of computer program instructions, stored in memory 902, to perform various operations, processes, methods disclosed herein.

The image processor 901 may be communicatively coupled to the memory 902 and configured to execute computer-executable instructions stored therein. The memory 902 may include a read only memory (ROM), a flash memory, random access memory (RAM), a dynamic random-access memory (DRAM) such as synchronous DRAM (SDRAM) or Rambus DRAM, a static memory (e.g., flash memory, static random access memory), etc., on which computer executable instructions are stored in any format. In some embodiments, the memory 902 may store computer-executable instructions of one or more image processing program(s) 903. The computer program instructions can be accessed by the image processor 901, read from the ROM, or any other suitable memory location, and loaded in the RAM for execution by the image processor 901. For example, memory 902 may store one or more software applications. Software applications stored in the memory 902 may include, for example, an operating system (not shown) for common computer systems as well as for soft-controlled devices.

Further, memory 902 may store an entire software application or only a part of a software application (e.g. the image processing program (s) 903) to be executable by the image processor 901. In addition, the memory 902 may store a plurality of software modules, for implementing the respective steps of the method for anatomical tree structure analysis consistent with the present disclosure. For example, the analysis model generation unit 202, the analysis model training unit 203, the analysis unit 204, and the model input extraction unit 205 (as shown in FIG. 2), may be implemented as soft modules stored on the memory 902. For another example, at least the analysis unit 204 and the model input extraction unit 205 may be implemented as soft modules stored on the memory 902, the analysis model generation unit 202 and analysis model training unit 203 may be located remote from the anatomical tree structure analyzing system 900 and communicate with the analysis unit 204 to enable it receive the updated analysis model, which may be generated by the analysis model generation unit 202 on the basis of the particular task and trained by the analysis model training unit 203 with the training sample from the training sample database 204 (in an off-line training process) and/or from the analysis unit 204 (i.e., the analysis results automatically or semi-automatically generated therefrom (with or without manual correction by the user) together with the corresponding extracted model inputs) (in an on-line training process).

Besides, the memory 902 may store data generated/buffered when a computer program is executed, for example, medical image data 904, including the medical images transmitted from image acquisition device(s), medical image database 905, image data storage device 906, etc. In some embodiments, medical image data 904 may include the received image(s) of the vessel tree, for which centerline extraction and 3D model reconstruction, the automatic geometrical feature extraction (as model inputs) and further image analysis (e.g., vessel stenosis degree prediction results) are to be implemented by the image processing program(s) 903. In some embodiment, medical image data 904 may include the received volumetric image of the vessel tree, for which the automatic geometrical feature extraction (as model inputs) and further image analysis (e.g., vessel stenosis degree prediction results) are to be implemented by the image processing program(s) 903. In some embodiments, the memory 902 may load a batch of training samples from the medical image database 905 and temporarily store the same as medical image data 904, to be utilized by the analysis model training unit 203 for mini-batch training. In some embodiments, the memory 902 may store temporarily the automatic image analysis results associated with the actual model inputs as on-line training samples. The training samples stored as the medical image data 904 may be cancelled after the training utilizing the same is complete, to release the space of the memory 902 and improve its capacity and performance.

In some embodiments, the generated analysis model for a task may be stored in the medical image data 904 and may be used (after trained) in the next image analysis of the same task. In some embodiments, the updated and optimized parameters of the trained analysis model may be stored in the medical image data 904, which may then be used in the next image analysis of the same task on the same patient. As an example, confronting a task of a coronary vessel stenosis degree prediction, the image processor 901 may retrieve the corresponding prediction model already generated and/or trained from the medical image data 904 and make use of the same (e.g. use it upon transforming training based on new training samples). As another example, confronting a task of a coronary vessel stenosis degree prediction on the same patient, the image processor 901 may retrieve the prediction model latest updated for the same patient from the medical image data 904 and use it directly.

In some embodiments, the image processor 901, upon performing an image analysis task, may associate the images of the tree structure together with the analysis results as medical image data 904 for presenting and/or transmitting. In some embodiments, the tree structure images together with the analysis results, e.g., the vessel tree images and lumen refine segmentation results, may be displayed on the image display 909 for the user's review. For example, the image display 909 may be an LCD, a CRT, or an LED display. In this manner, the user may confirm and correct the displayed analysis results by means of the input/output 907, if necessary. And the confirmed and corrected image analysis results may be temporarily stored associated with the model inputs as medical image data 904 in the memory 902 and may be transmitted to the medical image database 905, to be accessed, obtained, and utilized by other medical devices (e.g. other anatomical tree structure analyzing devices 900), if needed.

In some embodiments, the memory 902 may communicate with the medical image database 905 to transmit and save the extracted model inputs associated with the automatically or semi-automatically obtained analysis results into the same as a piece of training data, which may be used for off-line training. In this manner, the training sample database 204 as shown in FIG. 2 may be incorporated into the medical image database 905.

Besides, the parameters of the generated and/or trained analysis model may be stored in the medical image database 905, to be accessed, obtained, and utilized by other anatomical tree structure analyzing devices 900, if needed. In some embodiments, the neural network library 201 as shown in FIG. 2 may be included in the medical image database 905, so that the analysis model generation unit 202, if included as the image processing program(s) 903, may retrieve encoders and/or tree structured RNNs from the neural network library 201 in the medical image database 905.

In some embodiments, the medical image database 206 as shown in FIG. 2 may be incorporated into the medical image database 905, which may maintain medical images and/or 3D models and/or skeleton lines of the anatomical tree structures in accordance with patients. Thereby, the memory 902 may communicate with the medical image database 905 to obtain the images and/or 3D models and/or skeleton lines of the anatomical tree structure of the current patient.

In some embodiments, the image data storage device 906 may be provided to exchange image data with the medical image database 905. For example, the image data storage device 906 may reside in other medical image acquisition devices, e.g., a CT which performs volumetric scan on the patients. The volumetric images of the patients may be transmitted and saved into the medical image database 905, and the anatomical tree structure analyzing device 900 may retrieve volumetric images and analysis models of a specific patient from the medical image database 905 and make image analysis on the basis of the same.

The input/output 907 may be configured to allow the anatomical tree structure analyzing device 900 to receive and/or send data. The input/output 907 may include one or more digital and/or analog communication devices that allow the device 900 to communicate with a user or other machine and device. For example, the input/output 907 may include a keyboard and a mouse that allow the user to provide an input, including but not limited to task option, sampling position option, model input option, etc., as shown in FIG. 2.

The network interface 908 may include a network adapter, a cable connector, a serial connector, a USB connector, a parallel connector, a high-speed data transmission adapter such as optical fiber, USB 9.0, lightning, a wireless network adapter such as a Wi-Fi adapter, a telecommunication (9G, 4G/LTE, etc.) adapters. The device 900 may be connected to the network through the network interface 908. The network may provide the functionality of local area network (LAN), a wireless network, a cloud computing environment (e.g., software as a service, platform as a service, infrastructure as a service, etc.), a client-server, a wide area network (WAN), and the like.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or non-recordable media (e.g., read-only memory (ROM), random access memory (RAM), disk storage media, optical storage media, flash memory devices, etc.).

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

In this document, the terms "a", "an", and "the" are used, as is common in patent documents, to include one or more than one, independent of any other instances or usages of "at least one" or "one or more." Thus, for example, reference to "a level" includes a plurality of such levels, and so forth.

In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended. That is, the term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim. An apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Exemplary Methods described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub combinations of A, B, C, and D.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for an anatomical tree structure analysis, comprising the following steps:
receiving a task of the anatomical tree structure analysis;
setting, by a processor, a set of positions in an anatomical tree structure, wherein the anatomical tree structure represents a vessel or an airway;
determining, by the processor, a model input at each position among the set of positions on the basis of the task;
selecting, by the processor, an encoder for each position on the basis of the task, wherein the encoder is configured to receive the model input at each position and extract features for the corresponding position;
constructing, by the processor, a tree structured recurrent neural network (RNN) with nodes corresponding to the set of positions, by selecting an RNN unit for each node on the basis of the task and setting an information propagation among the nodes on the basis of spatial constraints of the set of positions in the anatomical tree structure, wherein each encoder is connected with the corresponding node of the tree structured RNN; and
providing the tree structured RNN for performing the task of the anatomical tree structure analysis.

2. The method of claim 1, wherein setting a set of positions in the anatomical tree structure comprises:
extracting a skeleton line of the anatomical tree structure and branches of bifurcation points therein; and
setting the bifurcation points and at least one point in each branch other than the bifurcation points as the set of positions.

3. The method of claim 1, wherein selecting the model inputs on the basis of the task comprises: when the task is any one of abnormality detection, abnormality classification, or parameter quantification, selecting image patches or feature vectors as the model inputs.

4. The method of claim 1, wherein selecting an encoder on the basis of the task comprises: when the task is any one of abnormality detection, abnormality classification, or parameter quantification, selecting at least one of a convolutional neural network (CNN), a fully convolutional neural network (FCN), and a multi-layer perceptron (MLP) as the encoder.

5. The method of claim 1, wherein selecting the RNN unit for each node on the basis of the task comprises: when the task is any one of abnormality detection, abnormality classification, or parameter quantification, selecting a long short-term memory (LSTM) or a gate recurrent unit (GRU) as the RNN unit.

6. The method of claim 1, wherein selecting the model inputs on the basis of the task comprises: when the task is segmentation, selecting image patches as the model inputs.

7. The method of claim 1, wherein selecting an encoder on the basis of the task comprises: when the task is segmentation, selecting a CNN or an FCN as the encoder.

8. The method of claim 1, wherein selecting the RNN unit for each node on the basis of the task comprises: when the task is segmentation, selecting a convolutional LSTM (CLSTM) or a convolutional GRU (CGRU) as the RNN unit.

9. The method of claim 1, wherein setting the information propagation among the nodes on the basis of the spatial constraints of the set of positions in the anatomical tree structure comprises:
setting a bidirectional information propagation between each pair of nodes corresponding to two adjacent positions in a path of the anatomical tree structure.

10. The method of claim 1, wherein setting the information propagation among the nodes on the basis of the spatial constraints of the set of positions in the anatomical tree structure comprises:
setting a unidirectional information propagation from a distal side to a root between at least one pair of nodes corresponding to two adjacent positions in a path of the anatomical tree structure.

11. The method of claim 1, further comprising:
training, by the processor, the model by using training samples corresponding to the task of the anatomical tree structure analysis.

12. The method of claim 11, wherein training the model comprises jointly optimizing parameters of the encoders and the tree structured RNN.

13. A computer-implemented method for an anatomical tree structure analysis, comprising:
receiving an anatomical tree structure image acquired by an image acquisition device, wherein the anatomical tree structure represents a vessel or an airway;
receiving an analysis model for a task of the anatomical tree structure analysis, the analysis model is constructed by connecting encoders for a set of positions in the anatomical tree structure with corresponding nodes of a tree structured recurrent neural network (RNN), wherein the nodes correspond to the set of positions, wherein a model input, the encoder, and an RNN unit of each node are selected based on the task, and an information propagation among the nodes are set based on spatial constraints of the set of positions in the anatomical tree structure;
calculating, by a processor, model inputs at the set of positions in the anatomical tree structure image; and
performing, by the processor, the task of the anatomical tree structure analysis by applying the analysis model to the calculated model inputs.

14. The method of claim 13, wherein the set of positions are along a skeleton line of the anatomical tree structure and include bifurcation points.

15. A system for an anatomical tree structure analysis, comprising:
an interface, configured to receive an anatomical tree structure image acquired by an image acquisition device, wherein the anatomical tree structure represents a vessel or an airway; and
a processor, which is configured to:
receive a task of the anatomical tree structure analysis;
set a set of positions in the anatomical tree structure;
determine a model input at each position among the set of positions on the basis of the task;
select an encoder for each position on the basis of the task, the encoder is configured to receive the model input at each position and extract features for the corresponding position;
construct a tree structured RNN with nodes corresponding to the set of positions, by selecting an RNN unit for each node on the basis of the task, setting an information propagation among the nodes on the basis of the spatial constraints of the set of positions in the anatomical tree structure, and connecting the nodes of the tree structured RNN with the respective encoders; and
provide the tree structured RNN for performing the task of the anatomical tree structure analysis.

16. The system of claim 15, wherein the processor is further configured to train the tree structured RNN using training samples corresponding to the task.

17. The system of claim 16, wherein the processor is further configured to:
- extract the selected model inputs at the set of positions from the anatomical tree structure image; and
- perform the task of the anatomical tree structure analysis using the trained model on the basis of the extracted model inputs at the set of positions.

18. The system of claim 15, wherein the processor is further configured to:
- extract a skeleton line of the anatomical tree structure from the acquired anatomical tree structure image; and
- present the extracted skeleton line on a user interface for a user to set the set of positions.

19. The system of claim 15, wherein the processor is further configured to:
- extract a skeleton line and branches of bifurcation points therein from the acquired anatomical tree structure image; and
- set the bifurcation points and at least one point in each branch other than the bifurcations as the set of positions.

20. A non-transitory computer readable medium having instructions stored thereon, the instructions, when executed by a processor, perform a method for an anatomical tree structure analysis, comprising the following steps:
- receiving a task of the anatomical tree structure analysis;
- setting a set of positions in an anatomical tree structure, wherein the anatomical tree structure represents a vessel or an airway;
- determining a model input at each position among the set of positions on the basis of the task;
- selecting an encoder for each position on the basis of the task, the encoder is configured to receive the model input at each position and extract features for the corresponding position;
- constructing a tree structured RNN with nodes corresponding to the set of positions, by selecting an RNN unit for each node on the basis of the task, setting an information propagation among the nodes on the basis of the spatial constraints of the set of positions in the anatomical tree structure, and connecting the nodes of the tree structured RNN with the respective encoders; and
- providing the tree structured RNN for performing the task of the anatomical tree structure analysis.

* * * * *